United States Patent [19]

Inouye et al.

[11] Patent Number: 4,653,331
[45] Date of Patent: Mar. 31, 1987

[54] TEST APPARATUS FOR UNIFORM TENSIONING OF LONG LENGTHS OF SMALL CABLES IN SIMULATED ENVIRONMENTS

[75] Inventors: Alan T. Inouye, Ventura; Jeffrey V. Wilson; Mark L. Baker, both of Camarillo, all of Calif.

[73] Assignee: The United States of America as represented by the Secretary of the Navy, Washington, D.C.

[21] Appl. No.: 876,618

[22] Filed: Jun. 20, 1986

[51] Int. Cl.⁴ .......................... G01L 1/24; G01N 3/10
[52] U.S. Cl. ........................................ 73/800; 73/826; 73/865.6
[58] Field of Search ................ 73/800, 829, 826, 831, 73/833, 837, 859, 860, 865.6

[56] References Cited

U.S. PATENT DOCUMENTS

| | | | |
|---|---|---|---|
| 2,942,455 | 6/1960 | Smith | 73/837 |
| 4,286,469 | 9/1981 | Trias | 73/829 |
| 4,346,601 | 8/1982 | France | 73/160 |
| 4,495,809 | 1/1985 | Higginbotham et al. | 73/865.6 |
| 4,505,540 | 3/1985 | Furusawa et al. | 350/96.21 |

FOREIGN PATENT DOCUMENTS

| | | | |
|---|---|---|---|
| 2856183 | 7/1980 | Fed. Rep. of Germany | 73/800 |
| 0061933 | 4/1982 | Japan | 73/826 |
| 0086740 | 5/1982 | Japan | 73/826 |
| 0968682 | 10/1982 | U.S.S.R. | 73/800 |

OTHER PUBLICATIONS

"Testing Optic Fibers", IBM Disclosure Bulletin, vol. 8, No. 6, Nov. 1965.

*Primary Examiner*—Stewart J. Levy
*Assistant Examiner*—Robert R. Raevis
*Attorney, Agent, or Firm*—Louis B. Allahut; Joseph M. St. Amand

[57] ABSTRACT

A means is provided to uniformly tension long lengths of small cables while they are simultaneously exposed to simulated environments such as deep ocean conditions. Tension on the cable is adjustable by varying the pressure inside an elastic bladder sealed about a stress spool on which the cable is wrapped, within a pressure chamber. Spool cores can be nested so that several lengths of different cables can be tested together.

16 Claims, 9 Drawing Figures

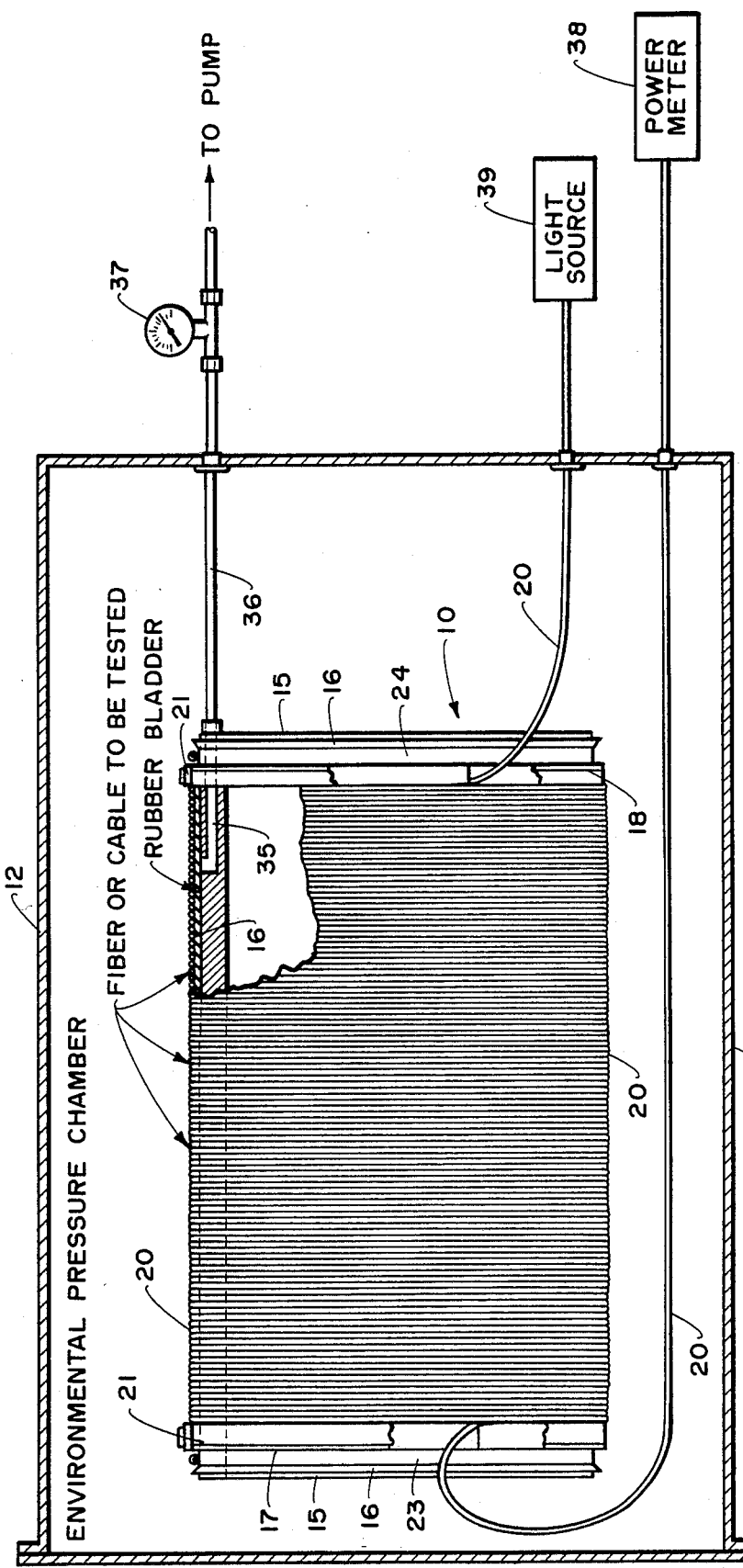

TEST APPARATUS FOR UNIFORM TENSIONING OF LONG LENGTHS OF SMALL CABLES IN SIMULATED ENVIRONMENTS

BACKGROUND OF THE INVENTION

This invention relates to test apparatus, and more particularly to a system for uniformly tensioning long lengths of small diameter cables, up to several kilometers in length, while simultaneously exposed to simulated environments such as deep ocean conditions.

As fiber optic cable technology has evolved there has been an increasing interest in applying that technology to cables for use in the deep ocean. Testing has shown that optical fibers, because of the brittle nature of the glass, are subject to static fatigue when exposed to seawater and under strain. The glass will fail through brittle fracture at strains/stresses well below its normal limits because of corrosion effects in micro cracks on the fiber surface. Ocean cable designs are attempting to eliminate this problem by both removing the fiber from exposure to seawater (by using sealing jackets, tubes, etc.) and by adding strengthening members to reduce or eliminate strain in the fibers. There is a definite need to verify long-term performance of fiber optic cables for use in the ocean under high pressure, low temperature, and sustained cable strain in tension.

Before committing to production of thousands of kilometers of such cable envisioned for ocean systems, it is necessary to verify the performance of the completed cables under simulated conditions. In order to obtain accurate optical attenuation measurements on the low-loss cables currently available it is necessary to have continuous cable lengths of at least a kilometer or more under test. To simply stretch out such a length of cable in a linear ocean simulation facility would require extremely expensive new pressure testing facilities. There is presently no method for testing adequate lengths of cable without major expense in building very long pressure vessels. A means to uniformly tension these small cables while also efficiently packaging them into existing pressure vessel facilities is needed to provide significant cost savings.

It is an object of the present invention to provide an efficient system for uniformly tensioning long lengths of small fiber optic cables in simulated deep ocean conditions.

SUMMARY OF THE INVENTION

An exemplary embodiment of the invention provides for wrapping long lengths of small cable about a thin bladder which is sealed to the outside of a stiff cylinder within a pressure vessel and pressurizing the bladder to uniformly tension the cable length while undergoing simulated deep ocean environment within the pressure vessel.

DESCRIPTION OF THE DRAWINGS

FIG. 1 is an elevational view of the cable testing device with partial cut away sections.

FIG. 5 is a free body diagram representing stress in the walls of a cylinder.

FIGS. 6a and 6b represent the cross-section of a thin wall and the cross-section of a layer of cable which approaches a thin wall cross-section.

FIG. 7 is a free body diagram representing stress in a single layer of wrapped cable which approaches the walls of a cylinder.

DESCRIPTION OF PREFERRED EMBODIMENT

The system for testing long cable lengths consists of a stress spool 10 which is placed within a pressure chamber 12, such as shown in FIG. 1, for example, where deep ocean conditions are simulated. Any suitable pressure vessel or environmental chamber can be used which will simulate the high pressure, low temperature, saline, etc. deep ocean type conditions.

Figure 2A:
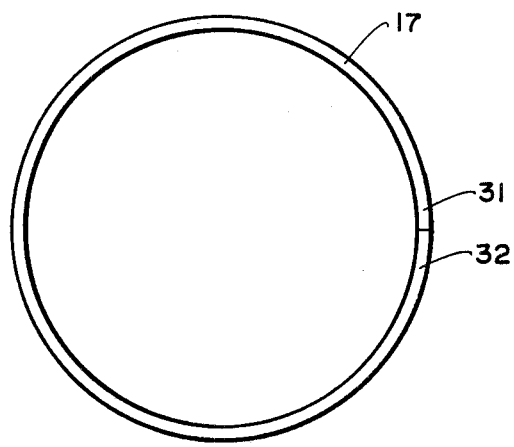
FIGS. 2a and 2b are a plan view and a side view, respectively, of a retaining ring for the device of FIG. 1.
Figure 2B:
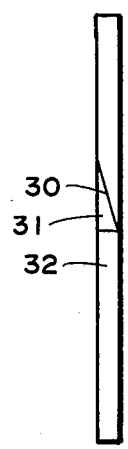
Figure 3:
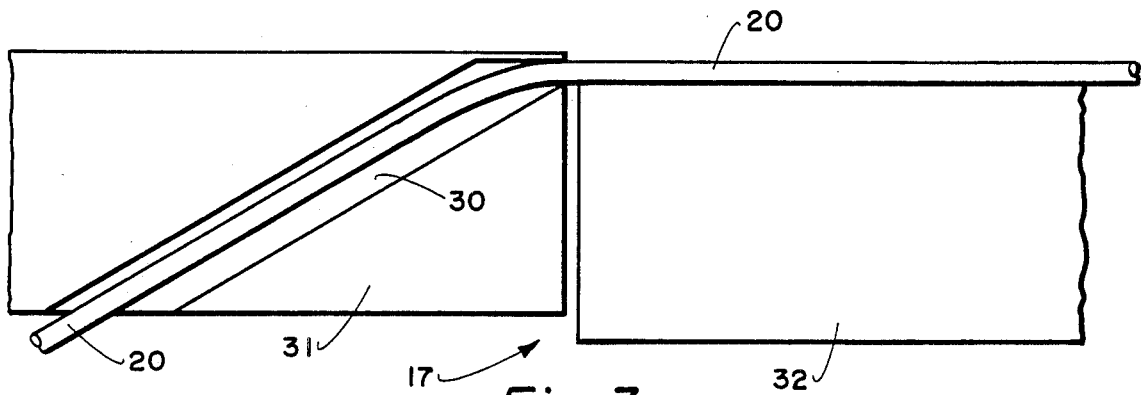
FIG. 3 is an enlarged partial view of the retaining ring of FIG. 2b.

Stress spool 10 comprises a stiff cylindrical core 15 having a thin bladder 16 fitted about the outside diameter of the cylinder. Cylindrical core 15 may be formed of thick walled pipe, for example. Bladder 16 is a cylindrical, thin-walled rubber boot which fits over cylindrical core 15. The bladder is anchored and sealed to the cylindrical core, at each end, with special bladder and cable retainers, comprised of clamped-on helix shoulders 17 and 18 and connectors 21. Simple hose type band clamp connectors 21 are used to secure the helix shoulders 17 and 18 to the spool core. The helix shoulders are also shown in FIGS. 2a and 2b, and FIG. 3. The bladder and cable retainers 17 and 18 are special in that, in addition to sealing the bladder to the cylindrical core, they prevent lateral movement of cable 20, when wound on the stress spool 10 (a single wound layer), and prevent the cable from slipping off the bladder.

Additional band clamps 23 and 24 can be used outboard of the special bladder retainers (i.e. clamped-on helix shoulders) 17 and 18, as shown in FIG. 1, to further aid in sealing bladder 16 to the spool core 15. Helix shoulders 17 and 18 also allow exit of the cable 20 without a gap between the last cable wrap and the clamps. A helix shoulder is shown in FIGS. 2a and 2b as a ring, formed from a band of metal for example, having an angled groove 30 allowing for a cable to exit the spool at a convenient angle. An enlarged view of the abutting ends 31 and 32 of the band which forms a helix shoulder 17 or 18 is shown in FIG. 3. End 31, for example includes groove 30 which allows for exiting the cable 20. Groove 30 in each shoulder ring is angled upward from the bottom surface of the helix shoulder and outward, as shown. Ends 31 and 32 are offset by the width of a cable 20 giving the shoulder ring a slight helical configuration, as can be seen best in FIG. 3. Opposite ends of cable 20 pass through sealed apertures in the pressure chamber wall to a power meter 38 and a light source 39, respectively, located outside the pressure chamber.

The spool core 15, for example, is made from about ½ inch wall thickness steel pipe. The thickness of the core is to minimize any yield of the core due to pressure of the bladder 16, when pressurized. Core 15, as shown in FIG. 1, is provided with hydraulic fittings 35 for pressurizing the bladder 16. An hydraulic line 36 connecting fitting 35 to a pressure source passes through a sealed fitting in the wall of pressure chamber 12 to a pressure gauge 37 and to a pump, not shown. Use of fluid to pressurize the elastic bladder will ensure uniform pressure, and hence stress, on each wound strand of cable 20.

The basic operating principle of the invention is related to the concept of fiber-wound construction for pressure vessels. It is known that in a thin-walled cylinder a relatively small internal pressure can produce very high stress in the walls, both in the longitudinal and the transverse directions. In the present invention, cable 20 is uniformly wrapped about thin bladder 16, which is sealed to the outside of rigid cylinder core 15. The space between the rigid cylinder core and the bladder is then pressurized, via hydraulic fitting 35, with a suitable fluid forcing the cable 20 to resist the pressure. Although the bladder itself resists some of the pressure, the cable elastic modulus is so much higher than the bladder that it dominates the behavior of the system and a simple test calibration can produce a very accurate relationship between the pressure applied and the tension/strain in the cable. The principal advantage to this approach is that the cable is tensioned uniformly along its length, while being bent at acceptably large radii of curvature that the tension approximates a pure linear tension very well. Power meter 38, and light source 39, located outside the pressure chamber, are used to measure change in optical attenuation of the cable, due to tension and pressure, as it undergoes tension and environmental stresses within chamber 12.

Figure 4:
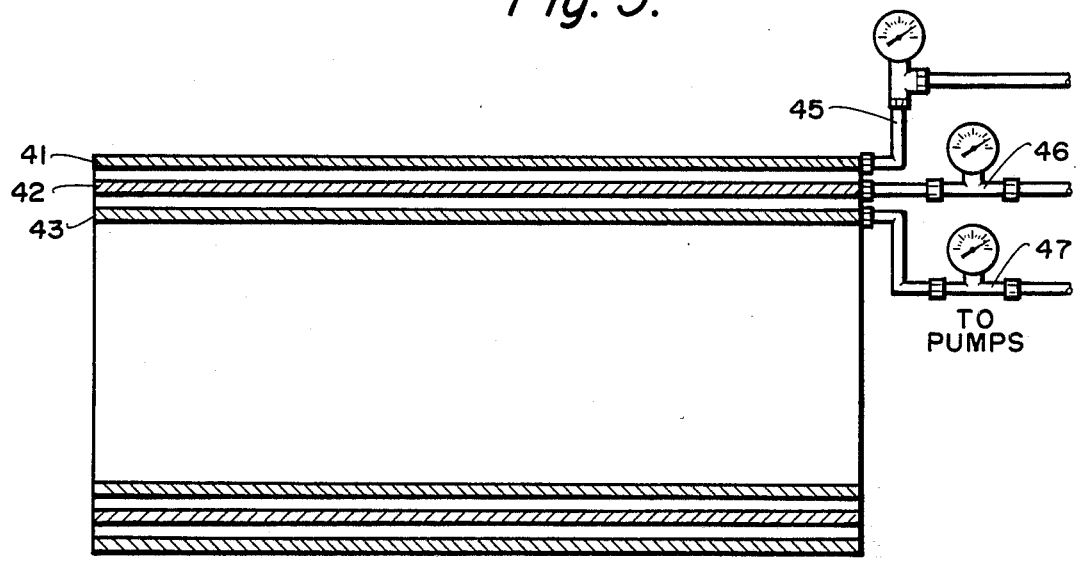
FIG. 4 schematically illustrates the nesting of three sizes of stress spools, as in FIG. 1, inside each other.

This system also allows for the nesting of several such stress spools in the same pressure vessel, as shown schematically in FIG. 4, by way of example, with bladder, clamps, and cable omitted for simplicity. Stress cylinders 41, 42 and 43 are nested one inside the other and connected to respective hydraulic pressurizing means 45, 46 and 47. With interconnection of the stress spool units it is possible to fit cable samples of several hundred meters length in standard 9-inch diameter pressure vessels and several kilometers length in an 18-inch diameter vessel.

The expandable spool system is based on the theory of stresses in thin-walled cylindrical vessels, whose wall thickness is less than 1/20 of their diameters. The assumption is that stress in the walls of the cylinder is uniform. Consider the free body diagram for a cylinder as shown in FIG. 5, where:

$T_c$ = circumferential tensile force
$\sigma_c$ = circumferential stress
$P_c$ = pressurized gas or liquid (force), which is
a product of internal pressure p and area WD.
Then,
$2T_c = P_c = pWD$ for equilibrium
$T_c = \sigma_c A = \sigma_c Wt$, (A = cross section area of wall)
therefore, $2\sigma_c Wt = pWD$, or $\sigma_c = pD/2t$ The cable on the spool can be looked at as a thin cylinder wall (FIG. 6a) by considering the cable wrapped about the spool, which is butted to adjacent wraps of cable on either side, as approaching a thin wall (see FIG. 6b) Then the thin wall becomes a free body diagram as shown in FIG. 7, but a correcting factor is required since the cable does not occupy the entire area of the thin wall, as can be seen when comparing FIGS. 6a and 6b. The difference is between the area of a square of height=t, and the area of a circle of diameter=t for each cable cross-section. The correction factor becomes: $(1 - \sigma/4) = 0.215$, or the area actually occupied by the cable (FIG. 6b) is 0.785 × the total thin wall area as represented by FIG. 6a. Hence, $\sigma_c = pD/2(0.785t)$ For cables in which the load-bearing members do not occupy the full cross-section, an additional correction is required and is added as specific cables are analyzed.

If a stress $\sigma_c$ is desired, and D and t are known, then p can be determined.

$p = 2(0.785t)\sigma_c/D$

For the spool of FIG. 1, described above, an example of strain test is as follows:
Desired 20,000 psi tensile load on the cable.
Core diameter = 16 inches.
Cable thickness = 2 mm × 0.03937 in/mm = 0.07874 in.

$p = 2(0.785t)\, \sigma_c/D$ $p = 2(0.785)\,(0.7874\text{ in})\,(20,000\text{ lbs/in}^2)/16\text{ in}$ $p = 154.5$ psi By pressurizing the bladder to 154.5 psi, circumferential stress $\sigma_c$ is anticipated to be 20,000 psi.

In the pressure vessel: At 10,000 psig ambient pressure on the cable, the bladder will be pressurized to 10,000 psig + 154.5 psig = 10,154.5 psig. As long as the delta p of the bladder is maintained at 154.5 psig, the tensile stress is expected to be maintained at 20,000 psi.

Other variables: Secondary effects from bulk compressibility and thermal strain of the core, pressurizing fluid, bladder, clamps and cable are evaluated to determine proper sequencing of loads.

The present system tensions the cable uniformly along its length while being bent at an acceptably large radii of curvature that the tension approximates a pure linear tension. Long lengths of small cable (up to several kilometers) can be uniformly tensioned while simultaneously being exposed to simulated deep ocean environments. By nesting several spool units together various lengths of different types of cables can be tested together. The expandable spool system is relatively light weight and utilizes space available in pressure vessels more efficiently than other tensioning devices, such as an assembly of sheaves and weights to tension the cable, and a long pressure vessel is not required. In addition, the system can be adapted for testing various types of small cables under various environmental conditions.

The helix shoulders 17 and 18 (i.e. split ring clamp device of FIGS. 2a and 2b) allows the cable to exit the wrap without leaving exposed areas of the bladder which can be a point where the bladder may protrude and rupture due to high pressures within the bladder. Overall, the device is simple and inexpensive to fabricate, and tension can be varied by simply changing the pressure in the bladder.

The material selection for use in the system depends on expected tensions required on the cables, intended system life, environment, and type of cables being tested. The dimensions of the system are dependent on the pressure chamber size or the desired test size of the cable.

Obviously many modifications and variations of the present invention are possible in the light of the above teachings. It is therefore to be understood that within the scope of the appended claims, the invention may be practiced otherwise than as specifically described.

What is claimed is:

1. A system for uniformly tensioning long lengths of small optical cables, up to several kilometers in length, while simultaneously being exposed to simulated environments, comprising:
   (a) an environmental chamber operable to be pressurized and in which various environmental conditions can be simulated;
   (b) at least one stress spool means within said environmental chamber; said stress spool means consisting of a rigid hollow cylinder means and a bladder means fitted about the outer diameter of said cylinder means; said bladder means operable to be expanded to apply tension to an optical cable wrapped about said stress spool means; clamped-on split ring means being provided at opposite ends of said hollow cylinder means to seal said bladder means to said hollow cylinder means and also to retain said said optical cable on said stress spool means such that lateral movement of said optical cable on said stress spool means is prevented and said optical cable is prevented from slipping off said stress spool means;
   said clamped-on split ring means comprising a helix shoulder having groove means for allowing exit of ends of said optical cable to said measuring means;
   (c) hydraulic means connected to said stress spool means to pressurize said bladder means for expansion thereof;
   (d) means for retaining on said stress spool means said optical cable wrapped thereon for testing purposes without leaving exposed areas of said bladder means where the bladder means can protrude and rupture due to high pressure within the bladder means; and
   (e) means for measuring any change in optical attenuation of said optical cable being tested due to tension and pressure exerted thereon;
wherein long sections of optical cable wound on said stress spool means can be uniformly tensioned on said stress spool means by prssurizing said bladder means via said hydraulic means and the tensioned optical cable can be measured for optical attenuation while undergoing various environmental conditions within said environmental chamber.

2. A system as in claim 1 wherein a plurality of said stress spool means of varying sizes are nested one within another in said environmental chamber for testing various sizes and lengths of optical cables.

3. A system as in claim 1 wherein said rigid hollow cylinder means is a thick walled metal pipe.

4. A system as in claim 1 wherein said hydraulic means is connected to a source of hydraulic pressure outside said environmental chamber.

5. A system as in claim 1 wherein said means for measuring change in optical attenuation of said optical cable undergoing testing is located outside said environmental chamber with ends of said optical cable passing through sealed apertures in the wall of said environmental chamber.

6. A system as in claim 1 wherein said means for retaining the optical cable on said stress spool means comprises a split ring of slight helical configuration.

7. A system as in claim 1 wherein said bladder means comprises a rubber boot which fits about said hollow cylinder means.

8. A system as in claim 1 wherein said bladder means is sealed to opposite ends of said hollow cylinder means by large hose type clamp means.

9. A system as in claim 1 wherein said split ring means comprises a metal band whose abutting ends are offset by a cable width.

10. A system as in claim 1 wherein said optical cable when wound on said stress spool means covers all exposed areas of said bladder means.

11. A system for uniformly tensioning long lengths of small cables, up to several kilometers in length, while simultaneously being exposed to simulated environments, comprising:
   (a) a stress spool means operable to be placed within an environmental chamber operable to be pressurized and in which various environmental conditions can be simulated; said stress spool means consisting of a rigid hollow cylinder means and an bladder means fitted about the outer diamter of said cylinder means; said bladder means operable to be expanded to apply tension to a cable when wrapped about said stress spool means; clamped-on split ring means being provided at opposite ends of said hollow cylinder means to seal said bladder means to said hollow cylinder means and also to retain said cable on said stress spool means such that lateral movement of said cable on said stress spool means is prevented and said cable is prevented from slipping off said stress spool means; said clamped-on split ring means comprising a helix shoulder having groove means for allowing exit of ends of said cable to said measuring means; said split ring means also comprising a metal band whose abutting ends are offset by a cable width;
   (b) hydraulic means connected to said stress spool means to pressurize said bladder means for expansion thereof;
   (c) means for retaining on said stress spool means cable wrapped thereon for testing purposes without leaving exposed areas of said bladder means where the bladder means can protrude and rupture due to high pressure within the bladder means; and
   (d) means for measuring any change in signal attenuation and operating conditions of said cable being tested due to tension, pressure, and environmental conditions exerted thereon;
wherein long sections of cable wound on said stress spool means can be uniformly tensioned on said stress spool means by pressurizing said bladder means via said hydraulic means and the tensioned cable can be measured for signal attenuation and other changes while undergoing various environmental conditions within said environmental chamber.

12. A system as in claim 11 wherein a plurality of said stress spool means of varying sizes are nested one within another in said environmental chamber for testing various sizes and lengths of cables.

13. A system as in claim 11 wherein said hydraulic means is connected to a source of hydraulic pressure outside said environmental chamber.

14. A system as in claim 11 wherein said means for retaining the cable on said stress spool means comprises a split ring of slight helical configuration.

15. A system as in claim 11 wherein said bladder means comprises a rubber boot which fits about said hollow cylinder means.

16. A system as in claim 11 wherein said cable when wound on said stress spool means covers all exposed areas of said bladder means.

* * * * *